(12) United States Patent
Park et al.

(10) Patent No.: US 8,333,803 B2
(45) Date of Patent: Dec. 18, 2012

(54) REINFORCED BIOLOGIC MATERIAL

(75) Inventors: Jason Park, Brooklyn, NY (US); Aaron Barere, Hoboken, NJ (US); Christopher T. Wagner, Flemington, NJ (US); Robert Kiefer, Quakertown, PA (US); E. Skott Greenhalgh, Lower Gwynedd, PA (US)

(73) Assignee: Lifecell Corporation, Branchburg, NJ (US)

( * ) Notice: Subject to any disclaimer, the term of this patent is extended or adjusted under 35 U.S.C. 154(b) by 345 days.

(21) Appl. No.: 12/621,890

(22) Filed: Nov. 19, 2009

(65) Prior Publication Data

US 2010/0161054 A1  Jun. 24, 2010

Related U.S. Application Data

(60) Provisional application No. 61/117,068, filed on Nov. 21, 2008.

(51) Int. Cl.
*A61F 2/08* (2006.01)
(52) U.S. Cl. .................................................. 623/13.14
(58) Field of Classification Search .... 623/13.11–13.14, 623/11.11, 14.12, 14.13; 606/232, 321, 317, 606/319; 600/30, 37
See application file for complete search history.

(56) References Cited

U.S. PATENT DOCUMENTS

| | | | | |
|---|---|---|---|---|
| 3,176,316 A * | 4/1965 | Bodell | | 623/13.19 |
| 3,463,158 A | 8/1969 | Schmitt et al. | | |
| 3,545,008 A * | 12/1970 | Bader, Jr. | | 623/13.15 |
| 4,149,277 A * | 4/1979 | Bokros | | 623/13.2 |
| 4,187,558 A * | 2/1980 | Dahlen et al. | | 623/13.14 |
| 4,255,820 A * | 3/1981 | Rothermel et al. | | 623/13.11 |
| 4,345,339 A * | 8/1982 | Muller et al. | | 623/13.2 |
| 4,400,833 A * | 8/1983 | Kurland | | 623/13.17 |
| 4,455,690 A * | 6/1984 | Homsy | | 623/13.15 |
| 4,584,722 A * | 4/1986 | Levy et al. | | 623/13.15 |
| 4,599,084 A | 7/1986 | Nashef | | |
| 4,633,873 A | 1/1987 | Dumican et al. | | |
| 4,662,886 A * | 5/1987 | Moorse et al. | | 623/13.15 |
| 4,668,233 A * | 5/1987 | Seedhom et al. | | 623/13.11 |
| 4,713,075 A * | 12/1987 | Kurland | | 128/898 |
| 4,790,850 A * | 12/1988 | Dunn et al. | | 623/13.19 |
| 4,792,336 A * | 12/1988 | Hlavacek et al. | | 623/13.18 |
| 4,917,700 A * | 4/1990 | Aikins | | 623/13.19 |
| 4,946,377 A * | 8/1990 | Kovach | | 623/13.18 |
| 4,964,414 A * | 10/1990 | Handa et al. | | 607/116 |
| 5,002,583 A | 3/1991 | Pitaru et al. | | |
| 5,078,744 A | 1/1992 | Chvapil | | |
| 5,116,372 A | 5/1992 | Laboureau | | |

(Continued)

FOREIGN PATENT DOCUMENTS

WO    WO 00/16822    3/2000

(Continued)

OTHER PUBLICATIONS

International Search Report and Written Opinion for PCT/US2009/065080 mailed Jul. 15, 2010, from the International Searching Authority of the Korean Intellectual Property Office.

(Continued)

*Primary Examiner* — Alvin J. Stewart
(74) *Attorney, Agent, or Firm* — Finnegan, Henderson, Farabow, Garrett & Dunner LLP

(57) ABSTRACT

The present disclosure provides an implantable medical device comprising a composite graft material including a first biologic component, such as an acellular tissue matrix, and a second non-biologic component.

13 Claims, 10 Drawing Sheets

U.S. PATENT DOCUMENTS

| | | | |
|---|---|---|---|
| 5,197,983 A * | 3/1993 | Berman et al. | 623/13.2 |
| 5,217,495 A * | 6/1993 | Kaplan et al. | 623/13.18 |
| 5,263,984 A * | 11/1993 | Li et al. | 623/13.18 |
| 5,336,616 A | 8/1994 | Livesey et al. | |
| 5,364,756 A | 11/1994 | Livesey et al. | |
| 5,374,539 A * | 12/1994 | Nimni et al. | 435/68.1 |
| 5,376,118 A * | 12/1994 | Kaplan et al. | 623/23.72 |
| 5,425,766 A | 6/1995 | Bowald | |
| 5,514,181 A * | 5/1996 | Light et al. | 623/13.18 |
| 5,549,676 A * | 8/1996 | Johnson | 623/13.13 |
| 5,593,441 A * | 1/1997 | Lichtenstein et al. | 600/37 |
| 5,595,571 A | 1/1997 | Jaffe et al. | |
| 5,674,286 A | 10/1997 | D'Alessio et al. | |
| 5,693,085 A * | 12/1997 | Buirge et al. | 623/1.13 |
| 5,800,543 A * | 9/1998 | McLeod et al. | 623/13.2 |
| 5,855,619 A | 1/1999 | Caplan et al. | |
| 5,981,827 A * | 11/1999 | Devlin et al. | 623/23.51 |
| 6,203,572 B1 * | 3/2001 | Johnson et al. | 623/13.15 |
| 6,206,931 B1 * | 3/2001 | Cook et al. | 623/23.75 |
| 6,214,047 B1 * | 4/2001 | Melvin | 623/11.11 |
| 6,468,300 B1 * | 10/2002 | Freidberg | 623/1.13 |
| 6,592,622 B1 | 7/2003 | Ferguson | |
| 6,592,623 B1 * | 7/2003 | Bowlin et al. | 623/14.13 |
| 6,599,319 B2 * | 7/2003 | Knudsen et al. | 623/13.11 |
| 6,638,312 B2 * | 10/2003 | Plouhar et al. | 623/23.72 |
| 6,699,286 B2 * | 3/2004 | Sklar | 623/13.17 |
| 6,733,510 B1 * | 5/2004 | Melvin | 606/148 |
| 6,746,483 B1 * | 6/2004 | Bojarski et al. | 623/13.14 |
| 6,802,862 B1 * | 10/2004 | Roger et al. | 623/13.14 |
| 6,827,743 B2 * | 12/2004 | Eisermann et al. | 623/23.54 |
| 6,884,428 B2 | 4/2005 | Binette et al. | |
| 6,893,462 B2 * | 5/2005 | Buskirk et al. | 623/13.17 |
| 6,905,517 B2 * | 6/2005 | Bonutti | 623/23.63 |
| 6,946,003 B1 | 9/2005 | Wolowacz et al. | |
| 7,070,558 B2 * | 7/2006 | Gellman et al. | 600/37 |
| 7,108,717 B2 * | 9/2006 | Freidberg | 623/1.41 |
| 7,163,563 B2 * | 1/2007 | Schwartz et al. | 623/23.76 |
| 7,252,832 B1 | 8/2007 | Stone et al. | |
| 7,513,910 B2 * | 4/2009 | Buskirk et al. | 623/13.17 |
| 7,674,289 B2 * | 3/2010 | Xu | 623/13.11 |
| 7,727,278 B2 * | 6/2010 | Olsen et al. | 623/13.12 |
| 7,799,076 B2 * | 9/2010 | Sybert et al. | 623/13.17 |
| 7,799,089 B2 * | 9/2010 | Plouhar et al. | 623/23.72 |
| 7,824,447 B2 * | 11/2010 | Xu | 8/94.1 R |
| 7,901,455 B2 * | 3/2011 | Koob et al. | 623/13.11 |
| 7,905,903 B2 * | 3/2011 | Stone et al. | 606/232 |
| 7,905,918 B2 * | 3/2011 | Cimino | 623/13.19 |
| 7,959,650 B2 * | 6/2011 | Kaiser et al. | 606/232 |
| 7,981,022 B2 * | 7/2011 | Gellman et al. | 600/30 |
| 7,981,023 B2 * | 7/2011 | Nowlin et al. | 600/30 |
| 8,007,533 B2 * | 8/2011 | Zhukauskas et al. | 623/13.14 |
| 8,025,896 B2 * | 9/2011 | Malaviya et al. | 424/423 |
| 8,052,753 B2 * | 11/2011 | Melvin | 623/13.14 |
| 2003/0035843 A1 | 2/2003 | Livesey et al. | |
| 2003/0143207 A1 | 7/2003 | Livesey et al. | |
| 2003/0225355 A1 * | 12/2003 | Butler | 602/48 |
| 2004/0034418 A1 | 2/2004 | Li et al. | |
| 2004/0078090 A1 | 4/2004 | Binette et al. | |
| 2004/0267362 A1 * | 12/2004 | Hwang et al. | 623/13.15 |
| 2005/0028228 A1 | 2/2005 | McQuillan et al. | |
| 2005/0159822 A1 | 7/2005 | Griffey et al. | |
| 2006/0073592 A1 | 4/2006 | Sun et al. | |
| 2006/0127375 A1 | 6/2006 | Livesey et al. | |
| 2006/0210960 A1 | 9/2006 | Livesey et al. | |
| 2007/0129811 A1 | 6/2007 | Plouhar et al. | |
| 2007/0162124 A1 | 7/2007 | Whittaker | |
| 2007/0248575 A1 | 10/2007 | Connor et al. | |
| 2008/0027542 A1 | 1/2008 | McQuillan et al. | |
| 2009/0035289 A1 | 2/2009 | Wagner et al. | |
| 2009/0306790 A1 | 12/2009 | Sun | |

FOREIGN PATENT DOCUMENTS

WO    WO 03/101312 A1    12/2003

OTHER PUBLICATIONS

Scott A. Klein et al. "Tendon Graft Fixation in ACL Reconstruction" *Acta Ortho Scand*, 75(1): 84-88 (2004).

Charles E. Butler et al. "Reduction of Abdominal Adhesions Using Composite Collagen-GAG Implants for Ventral Hernia Repair" *Plast Reconstr Surg.*, Aug.;114(2):464-73 (2004).

Charles E. Butler et al. "Reduction of Adhesions with Composite AlloDerm/Polypropylene Mesh Implants for Abdominal Wall Reconstruction" *J Biomed Mater Res.*, 58(1):75-80 (2001).

European Search Report issued in Patent Application No. 07797396.4, mailed Aug. 18, 2011.

Ge et al., "Biomaterials and scaffolds for ligament tissue engineering" *J. Biomed. Mater. Res.*, 77A:639-652 (2006).

International Search Report and Written Opinion issued in PCT/US2007/068607, mailed Sep. 12, 2008, from the International Searching Authority of the U.S. Patent & Trademark Office.

U.S. Office Action issued on Oct. 29: 2008, in U.S. Appl. No. 11/746,557, filed May 9, 2007 by McQuillan et al.

U.S. Office Action issued on Jul. 27, 2009, in U.S. Appl. No. 11/746,557, filed May 9, 2007 by McQuillan et al.

U.S. Office Action issued on Feb. 3, 2010, in U.S. Appl. No. 11/746,557, filed May 9, 2007 by McQuillan et al.

U.S. Office Action issued on Nov. 4, 2010, in U.S. Appl. No. 11/746,557, filed May 9, 2007 by McQuillan et al.

U.S. Office Action issued on Apr. 12, 2011, in U.S. Appl. No. 11/746,557, filed May 9, 2007 by McQuillan et al.

* cited by examiner

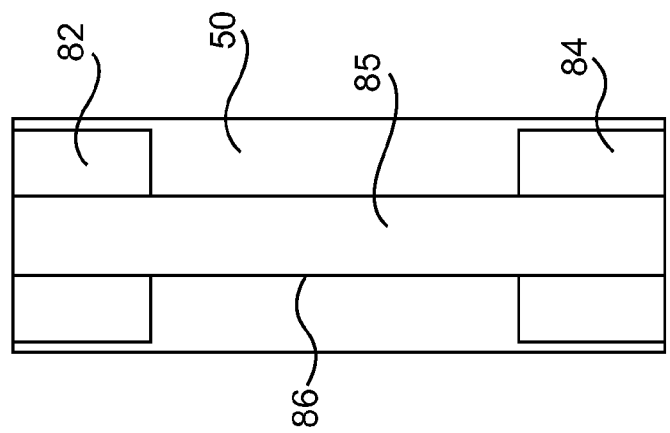
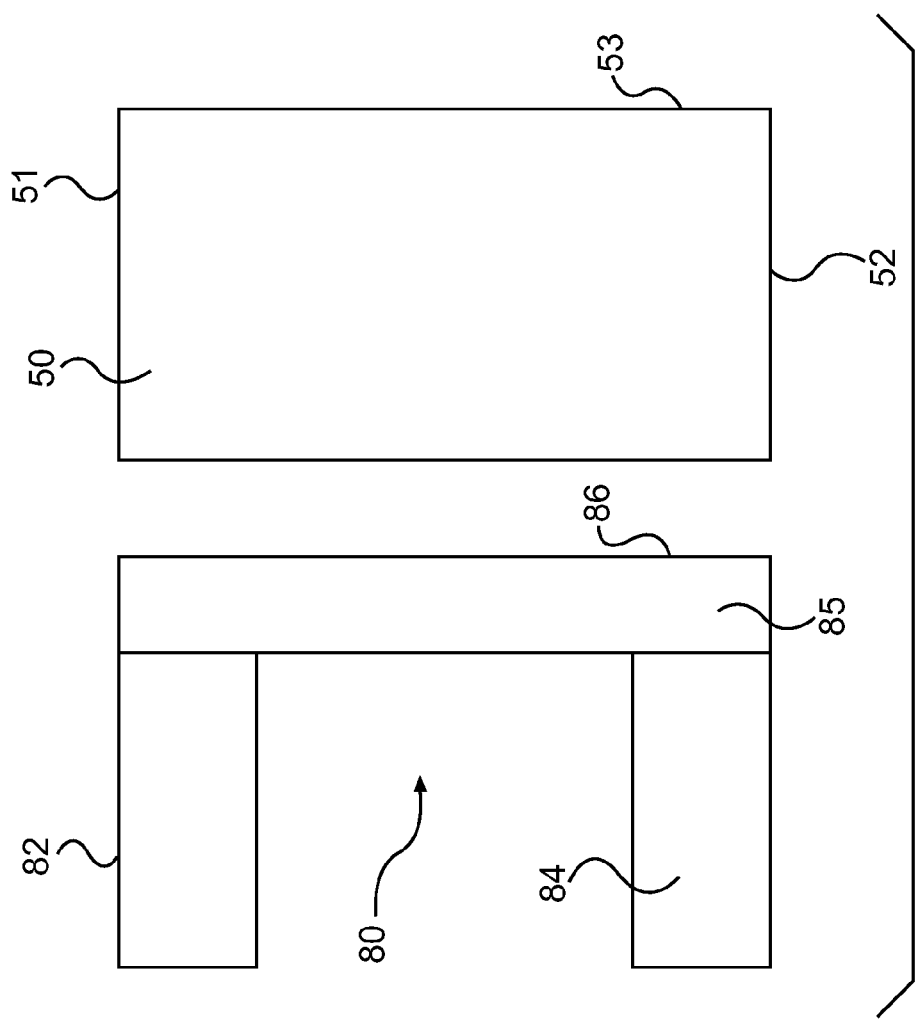

US 8,333,803 B2

REINFORCED BIOLOGIC MATERIAL

This application claims priority under 35 U.S.C. §119 to U.S. Provisional Patent Application No. 61/117,068, which was filed on Nov. 21, 2008.

The present disclosure generally relates to implantable medical devices and methods for making the same.

Surgeons performing ligament and tendon replacement in mammals have long sought a material that approximates the load transmission and performance of the native ligament and tendon structures. Synthetic ligaments and tendons have been made from steel, polyester, polyurethane, polyethylene, Nylons, polytetrafluoroethylene, carbon fiber and other man-made materials. Combinations of any one or more of the aforementioned materials have also been used to manufacture synthetic ligaments. However, synthetics typically experience decreasing functional capability over time and can wear out, fray, and/or particulate in relatively short time periods after implantation.

As an alternative to synthetic materials, natural ligament or tendon tissue harvested from autografts and/or allograft sources may also be used in ligament or tendon replacement procedures. As with synthetic materials, for both autografts and allografts, long-term recovery of functional parameters (e.g., failure load, linear and tangential stiffness, failure stress, and strain at failure) remains significantly reduced compared to native ligament, tendon or other soft tissue structures.

There is a need for a material for ligament, tendon, and other soft tissue repair and replacement that is free of donor site morbidity associated with autografts, has improved failure rates over traditional allografts and synthetic tissues, and better approximates native tissue biomechanical performance.

This discussion of the background disclosure is included to place the present disclosure in context. It is not an admission that any of the background material previously described was published, known, or part of the common general knowledge as at the priority date of the present disclosure and claims.

As used herein, the term, "comprise" and variations thereof, such as "comprising" and "comprises," is not intended to exclude other additives, components, integers or steps.

SUMMARY

In some embodiments, an implantable medical device is provided. The device comprises a plurality of first elongate non-biologic elements, at least a portion of which are under a tensile or compressive stress prior to implantation; at least one biologic component surrounding at least a portion of the plurality of first elongate elements; and at least one second elongate non-biologic element, wherein the at least one second element secures at least one end portion of the plurality of first elongate non-biologic elements.

In some embodiments, a method of making a composite prosthesis is provided. The method comprises providing a plurality of first elongate non-biologic elements; applying a load to the plurality of first elongate non-biologic elements; covering at least a portion of the plurality of first elongate non-biologic elements with at least one biologic component; and securing the plurality of first elongate non-biologic elements with at least one second elongate non-biologic element.

In some embodiments, an implantable medical device is provided. The device comprises at least one non-biologic core material under tensile stress; and at least one biologic element disposed about the at least one non-biologic core, the at least one biologic element comprising a biomatrix; wherein the at least one non-biologic core bears a greater tensile load at a time of implantation than the at least one biologic element, while transmitting stress to the at least one biologic element; and after implantation, the at least one non-biologic core gradually weakens, thereby dynamically transferring additional tensile load to the at least one biologic element.

In some embodiments, a method of making a composite prosthesis is provided. The method comprises providing at least one non-biologic core; applying a tensile load to the non-biologic core; and disposing at least one biologic element about the at least one non-biologic core, the at least one biologic element comprising a biomatrix; wherein the at least one non-biologic core bears a greater tensile load at a time of implantation than the at least one biologic element, while transmitting stress to the at least one biologic element; and after implantation, the at least one non-biologic core gradually weakens, thereby dynamically transferring additional tensile load to the at least one biologic element.

BRIEF DESCRIPTION OF THE DRAWINGS

FIG. 4A shows an exemplary embodiment of a composite graft material employing a non-biologic component in the form of a flat sheet.

FIG. 4B shows an exemplary embodiment of a rolled composite graft material.

DETAILED DESCRIPTION

Figure 1:
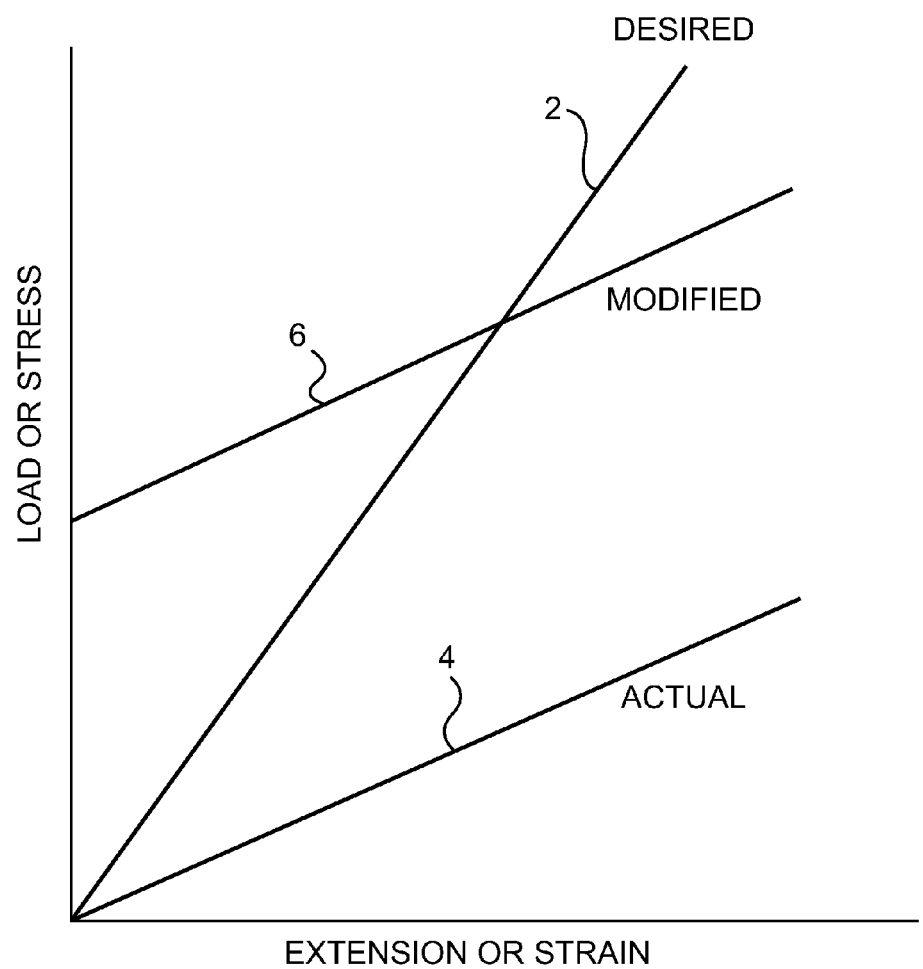
FIG. 1 is an exemplary stress-strain curve for various graft materials.

The present disclosure relates to implantable medical devices and methods of producing and using such devices. In certain embodiments, the medical devices include composite materials/tissues. In some embodiments, the composite materials comprise both biologic and non-biologic components suitable for use as a tissue implant or replacement for a ligament, tendon, or soft tissue structures. In some embodiments, the composite is constructed with at least two materials, for example, a non-biologic component (e.g., a synthetic polymer) and a biologic component (e.g., a biomatrix). In some embodiments, the non-biologic component is combined with the biologic component to create a composite tissue that utilizes certain properties of the constituent materials.

The non-biologic component, such as a synthetic polymer, is designed to provide appropriate mechanical properties to the composite structure immediately after implantation and to transmit higher loads over traditional biologic implants when the material is implanted. In some embodiments, the non-biologic component transmits some load and motion to the biologic component. In some embodiments, the biologic component is designed to assist in longer-term healing. In some embodiments, the motion/load distribution between the non-biologic component and the biologic component of the composite material contributes to an environment suited for tissue healing. In some embodiments, the biologic component, via a biomatrix, facilitates a process of becoming or transforming from a basic biologic tissue scaffold to a tissue similar to the native tissue being replaced (e.g., a ligament-like tissue) by encouraging or allowing the in-growth of native cells within the matrix structure of the biologic component.

Composite Material:

Tissue grafts generally experience some change or deterioration in mechanical characteristics within the first month after implantation. Such mechanical performance characteristics may include, for example, load performance, elasticity and stiffness. Recovery of some or all of the mechanical performance characteristics typically progresses over one to two years after implantation.

Generally, synthetic materials used in tissue replacement impart an initial load capacity at the time of implantation that can be equal to or higher than natural tissue implants. But, synthetic tissue implants typically experience a continual, and at times, significant loss in load capacity over the first two years after implantation.

Natural fiber tissue implants, such as autografts and allografts, experience a significant drop in load capacity soon after implantation, with an ultimate recovery of load capacity and other mechanical performance characteristics of between 50-60% of the starting capacity of the natural graft tissue.

In some embodiments, the composite graft material of the present disclosure combines the benefits of typical synthetic polymer tissue grafts (i.e., relatively high initial mechanical performance characteristics) with the prohealing and better long-term mechanical characteristics of natural tissue grafts. The composite tissue may, for example, perform as a summation of its individual components, or better than a summation of the individual components. For example, a typical synthetic implant experiences degradation with decreasing physical performance over time. The composite tissue of the present disclosure provides a layer of biomatrix around or over the synthetic component, which can result in slower degradation than would be exhibited by a typical, uncoated synthetic implant.

In some embodiments, the first biologic component and the second non-biologic component of the composite graft material are constructed to produce mechanical performance parameters desired for the specific tissue being replaced. For example, in constructing a composite material for ligament replacement, it may be desirable to have an ultimate load failure of approximately 1800N. If the constructed first component biomatrix material provides an ultimate failure load of only 400N, then the synthetic second component can be configured to provide the remaining 1400N to produce a composite graft material having the desired performance characteristics. Similarly, if the desired stiffness for the ACL replacement graft is 200N/mm and the biomatrix of the first component provides only 50N/mm, then the polymeric material of the second component can be configured to provide the remaining stiffness of 150 N/mm.

FIG. 1 illustrates an exemplary stress-strain curve of various materials. Line 2 illustrates a desired curve for an ideal graft. Line 4 illustrates an exemplary actual stress-strain curve for either a synthetic or natural tissue graft. As can be seen, the actual grafts are not capable of reaching the desired stress levels for the same amount of strain sought in a desired graft.

In some embodiments, the composite graft material described herein includes both a biologic and a non-biologic material (e.g., preparation of a weave, or of a braid or of a crimp, or of some other configuration such as a layered or rolled configuration), which raises the stress-strain curve for the composite graft material along the y axis. Consequently, line 6 illustrates a modified, composite graft materials having improved performance compared to synthetic or biologic grafts.

Figure 2:
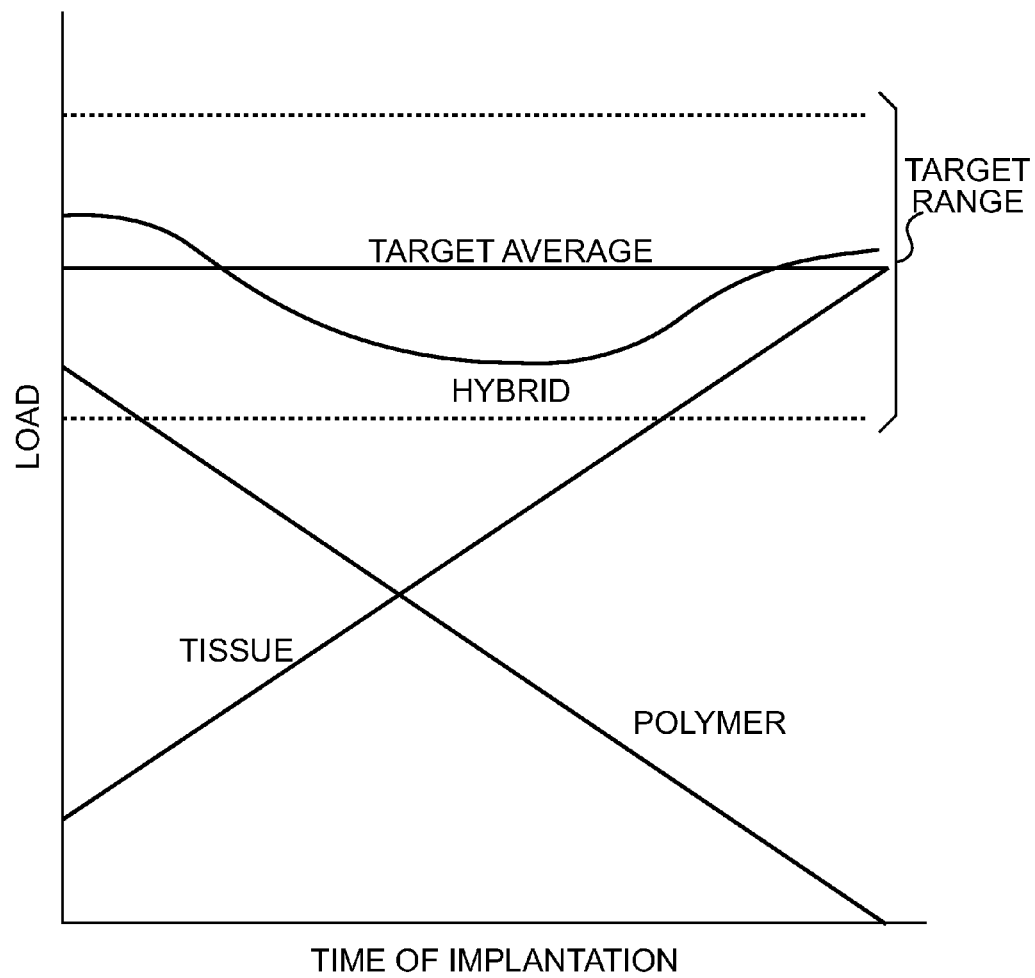
FIG. 2 is a graph illustrating the concept of functional target loading of a composite graft material.

FIG. 2 illustrates the load capacity versus time since implantation of the composite graft material to demonstrate the concept of functional target loading of the composite graft material. The biologic material alone has a relatively low load capacity at the time of implantation, but as the body subsequently heals, the load capacity of the biologic component increases over time. Conversely, a polymer graft's load-bearing capacity is relatively high at implantation, but decreases subsequently. It has been found that a composite graft material consistent with the present disclosure (labeled "Hybrid"), which comprises both a biologic component having a biomatrix and a non-biologic component (such as a polymer), has a relatively stable load-bearing capacity over time (that is, the load bearing capacity starts out, and remains, in the "Target Range").

The non-biologic component can be coupled with the biologic component in a variety of ways. For example, the biologic component may be disposed around the non-biologic component (as exemplified in FIG. 3), or vice versa. Alternatively, the biologic component may be embedded within a coating, a knit, weave, braid or other structure of the non-biologic component. To provide load sharing between the non-biologic component and the biologic component, the two components may, for example, be co-mingled or layered and rolled tightly around one another. In some embodiments, such structures create friction between the components. In some embodiments, compressive force is added to the layered construct, e.g., by including securing straps similar to a belt and hoop design.

Figure 3A:
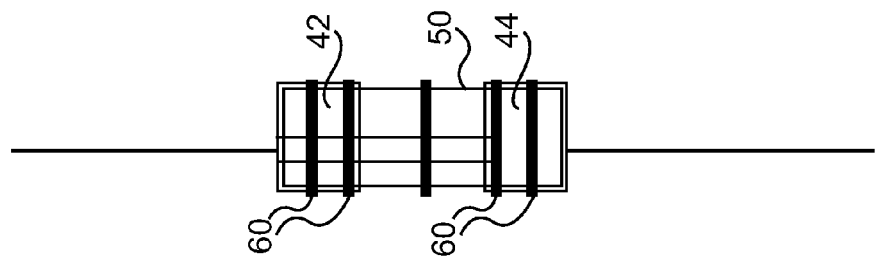
FIGS. 3 and 3A show an exemplary embodiment of a composite graft material.
Figure 3:
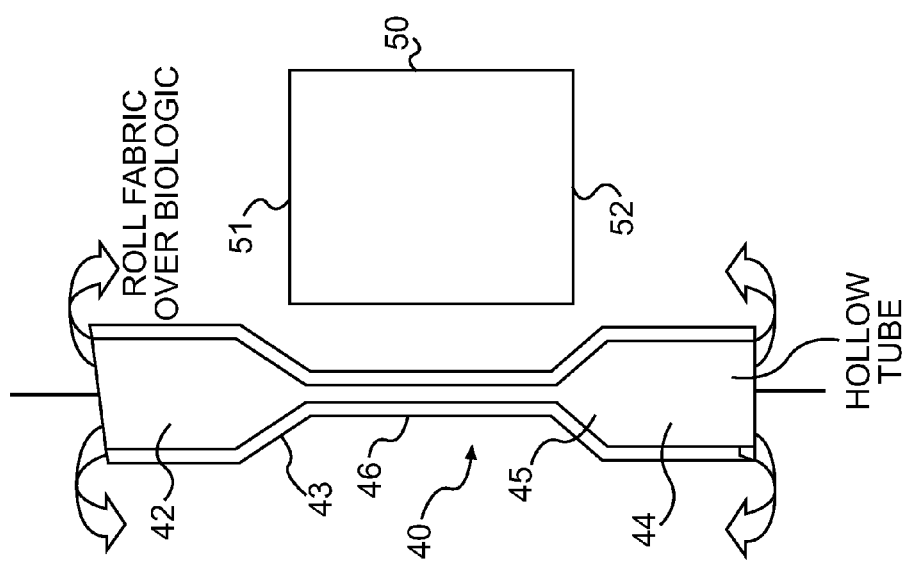

FIG. 3 depicts an exemplary embodiment of the composite graft material of the present disclosure. As shown, tubular non-biologic component 40 is provided having upper portion 42, upper taper region 43, lower portion 44, lower taper region 45, and neck portion 46. Biologic component 50 is also provided and is illustrated as a sheet with an upper edge 51 and a lower edge 52. In some embodiments, biologic component 50 is wrapped around neck portion 46 of non-biologic component 40 so that upper edge 51 is in contact proximal to or with upper taper region 43 and lower edge 52 is in contact proximal to or with lower taper region 45. Biologic component 50 can wrap or encircle neck portion 46 one or more times to form a multi-layer wrap. For example, biologic component 50 can wrap around neck portion 46 of non-biologic component 40 one time, two times, three times, four times, five times, or more. Biologic component 50 can similarly wrap around upper portion 42 and lower portion 43 of non-biologic component 40 one or more times.

In some embodiments, after wrapping biologic component 50 around non-biologic component 40, upper portion 42 of non-biologic component 40 may be rolled or folded over wrapped biologic component 50 and toward lower portion 44 such that at least some of upper portion 42 extends below the upper taper region 43 and overlaps neck portion 46. In some embodiments, lower portion 44 is rolled or folded over biologic component 50 and toward upper portion 42 such that at least some of lower portion 44 extends above lower taper region 45 and overlaps neck portion 46, as depicted in FIG. 3A.

In some embodiments, securing straps and/or tethers 60 are provided to apply compressive force to the rolled composite graft material and provide frictional contact between the biologic component and the non-biologic component. The securing straps may, for example, be constructed of the same material as non-biologic component 40. Tethers 60 may also be made from the same material as the non-biologic component of the composite material or from other materials such as stainless steel or non-bioabsorbable polymers.

Tethers 60 may be useful during implantation or construction of the composite graft material. For example, tethers 60 may be used to pull the composite graft material into a bone tunnel. Tethers 60 may also be used, for example, to anchor non-biologic component 40 while biologic component 50 is wrapped around non-biologic component 40.

Tethers 60 can be attached to non-biologic component 40 in various ways. For example, tethers 60 may be woven, knitted, or braided into non-biologic component 40. Tethers 60 may also be integrated into the non-biologic component 40, and may be configured to detach from non-biologic component 40. In some embodiments, tethers 60 are used as a radiopaque marker.

In some embodiments, a composite graft material in accordance with the present disclosure is constructed with a non-biologic component in the form of a flat sheet, as illustrated in FIG. 4A. Non-biologic component 80 includes upper portion 82, lower portion 84, neck portion 85, and neck lateral edge 86. Upper portion 82 and lower portion 84 may be made of same or different non-biologic material as neck portion 85. For example, neck portion 85 may comprise a high tensile strength textile of a bioabsorbable polymer, while upper portion 82 and lower portion 84 comprise a relatively low tensile strength textile of a bioabsorbable polymer. Non-biologic component 80 may also, for example, comprise non-textile polymers as previously described.

Referring still to FIG. 4A, biologic component 50 may, for example, be provided as a flat sheet of biologic material comprising an acellular tissue matrix having an upper edge 51, a lower edge 52, and a lateral edge 53. In some embodiments, non-biologic component 80 is placed on top of biologic component 50 such that neck lateral edge 86 of non-biologic component 80 aligns with lateral edge 53 of biologic component 50, and the two layered components are then rolled such that neck lateral edge 86 and lateral edge 53 remain aligned and form the innermost portion of the roll.

FIG. 4B shows a non-limiting embodiment of a rolled composite graft material in accordance with the present disclosure. This rolled composite graft material is constructed as described above, with the biologic component 50 forming the outside surface of the rolled structure and neck lateral edge 86 forming the inner most portion of the rolled structure. Upper portion 82 and lower portion 84 form a multi-layered non-biologic material within the rolled structure and can provide added strength and material to secure the composite graft material to surrounding native tissue, for example, by interference screws.

In some embodiments, the composite graft material is designed to match the size (length, width, thickness) of the natural structure (i.e., ligament or tendon) it will replace. For example, for an ACL, the composite graft material may be designed to be about 6 to 12 mm in diameter for a unibody device or 3 to 6 mm in diameter if separated into two bundles. It is known that within the body, specific ligament sizes slide and fit between bony structures. A ligament that is too small may not distribute stress evenly, and a ligament that is too large may interfere with or rub against one or both bony structures. Thus, matching the size of the implant material with the native tissue to be removed can reduce complications.

In some embodiments, the size of the composite graft material is customized to the patient and the tissue being replaced. For example, one or more rolls of biologic and non-biologic components can be added or removed by varying the size or length of the individual components. The longer the pre-rolled composite construct, the more rolls are possible, thereby producing a finished composite graft material having a greater diameter. Alternatively the number of layers of individual components can be altered to adjust the final size of the graft material. For example, a composite construct comprising a tissue layer, a polymer layer, and another tissue layer would provide a larger diameter graft than a composite construct of only two layers.

Figure 5:
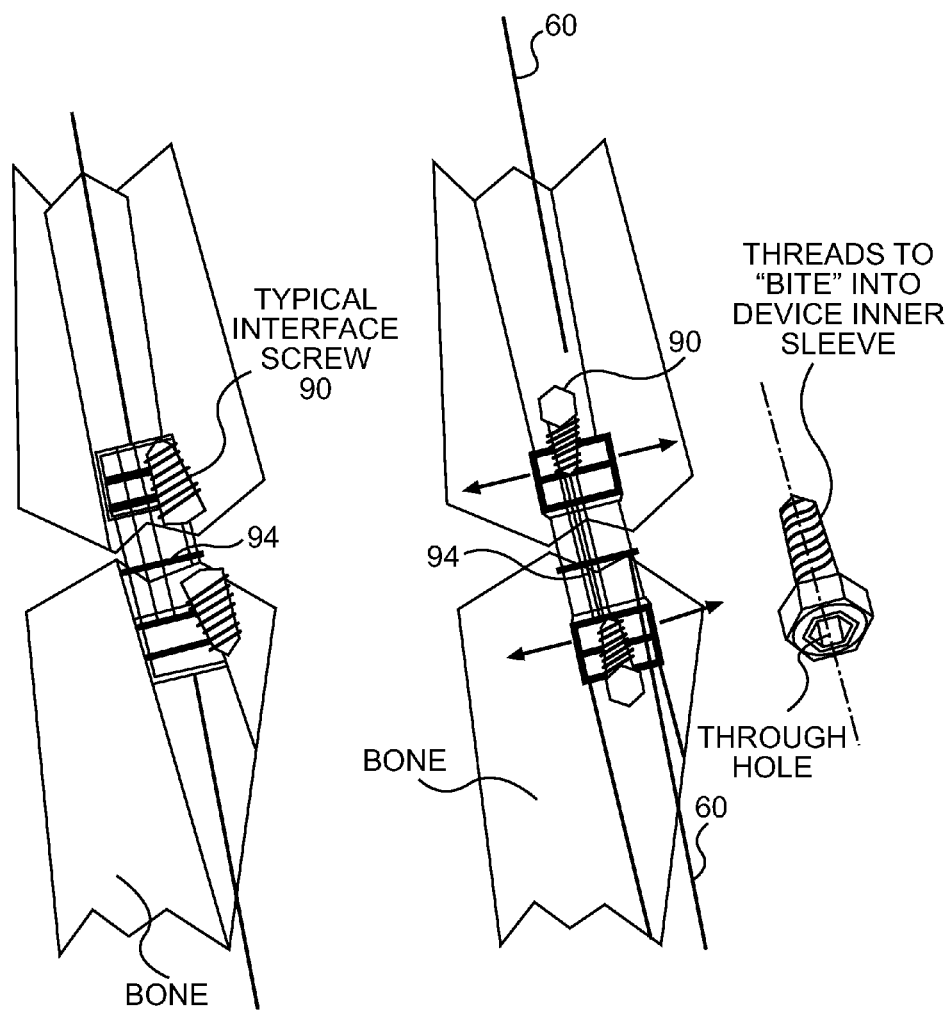
FIG. 5 shows an exemplary embodiment of an interference screw for anchoring a composite graft material.

Various techniques may be employed to anchor or fix the composite graft material to an implantation site. For example, in an ACL replacement, interference screws are used for anchoring cadaver or autograft materials. In some embodiments, an interference screw is provided that anchors the composite graft material. This is shown in FIG. 5, wherein interference screw 90 is inserted into the core of graft 94 such that as interference screw 90 advances, screw 90 expands the diameter of graft 94 to exert outwardly radial pressure against the surround bone tunnel. Other common fixation devices may be used, including cross-pins, endobuttons, sutures, or staples.

In some embodiments, screws or other anchoring devices can be made of titanium, stainless steel, biodegradable metals, biodegradable or bioabsorbable polymers such as polylactic acid (PLA), polyglycolic acid (PGA), polylactideglycolide acid (PLGA), polydioxanone (PDO), or polycaprolactone (PCL) As a non-limiting example of a typical interference screw, non-limiting mention is made of the RCI screw manufactured by Smith and Nephew, Andover Mass., 01810.

The biologic component comprising the biomatrix material of the disclosed composite graft material may benefit from the stress of ordinary movement following implantation. For example, the stresses and strains caused by ordinary activity may cause the biologic tissue to be stronger and recover to a greater ultimate strength due to normal remodeling facilitated by mechanical forces.

In some embodiments, the non-biologic component of the composite tissue graft material described herein is preloaded with a tensile load ranging from greater than 0N to about 1800N (e.g., from about 0.1 to about 1700N; about 10 to about 1600N, about 100 to about 1500N, about 150 to 1400, about 200 to 1300 etc.). The initial stress on strain on the non-biologic material is partially transferred to the biologic component, with the non-biologic component assuming more of the applied stress after reaching a preloaded limit.

As previously discussed, FIG. 1 illustrates an exemplary stress-strain curve of various tissue grafts. Line 2 illustrates a desired curve for an ideal graft. Line 4 illustrates an exemplary actual stress-strain curve for either a synthetic or natural tissue graft. As can be seen, natural grafts are not capable of reaching the desired stress levels for the same amount of strain sought in a desired graft. In contrast, because it incorporates both biologic and non-biologic materials, some embodiments of the composite graft materials described herein may exhibit a stress-strain curve that is shifted along the y axis. Consequently, line 6 of FIG. 1 illustrates a composite graft material having improved load capacity performance over actual synthetic or biologic grafts.

Figure 7:
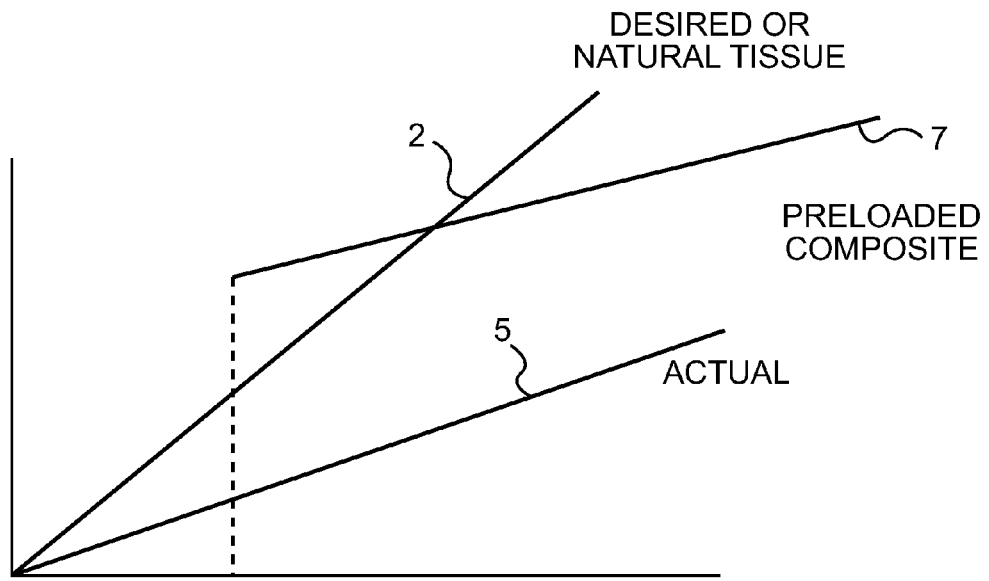
FIG. 7 is a graph illustrating the effect of pre-tensioning on the stress-strain curve of various graft materials, according to certain embodiments.

In some embodiments, the non-biologic component, the biologic component, or both the non-biologic and biologic components can be placed under tensile stress prior to implantation. This has the effect of moving the stress-strain curve of the material along the x-axis as depicted in FIG. 7. Line 2 illustrates a desired curve for an ideal graft material. Line 5 illustrates an actual curve for synthetic or natural tissue graft, and line 7 illustrates a curve of a composite graft material that has been subjected to preloading with a tensile stress.

In some embodiments, a portion of the tensile load applied to the non-biologic component is transferred to the biologic component. The initial strain applied is selected to be high enough to prevent or retard resorption of the biologic component upon implantation, but low enough to avoid physically damaging the biologic tissue. For example, the strain applied to the biologic component may range from less than or equal to 40%, less than or equal to 35%, less than or equal to 30%, less than or equal to 25%, less than or equal to 20%, less than or equal to 15%, less than or equal to 10%, less than or equal to 5%, and less than or equal to 1% of the initial strain applied to the non-biologic material by an initial tensile load. The initial strain applied to the biologic component may also fall within any range specified by a combination of the above recited endpoints, e.g., from greater than or equal to 1% to less than or equal to 40%, from greater than or equal to 5% to less than or equal to 35%, from greater than or equal to 10% to less than or equal to 30%, and from greater than or equal to 15% to less than or equal to 25% of the initial strain imparted to the non-biologic component by an initial tensile load.

In some embodiments, a composite graft material can be made using a plurality of elongate non-biologic components wrapped with at least one layer of a biologic component. The elongate non-biologic components can be placed under a tensile stress ranging from greater than 0N to 1800N (e.g., from about 100 to about 1700N; about 200 to about 1600N, about 300 to about 1500N, etc.), prior to wrapping with the biologic component. The plurality of elongate non-biologic components may also be pre-wrapped in a sheath comprising non-biologic components. At least one end of the non-biologic components can be secured (e.g., by whipping, wrapping, and/or winding) with an additional elongate component to form multiple layers with a raised surface at the end. The biologic component may, for example, be wrapped around the secured plurality of elongate non-biologic components and secured with a smaller fastening or whipping adjacent to the raised surface formed by the secured biologic component.

In some embodiments, all of the plurality of elongate non-biologic components can be placed under a tensile stress prior to forming the composite graft material. In other embodiments, a percentage of the elongate non-biologic components can be placed under tensile stress prior to forming the composite graft material, while a percentage of the elongate biologic components can be free of tensile stress prior to forming the composite graft material. Further, in some embodiments, the plurality of elongate non-biologic components and the biologic component can be placed under a tensile stress prior to final assembly of the graft.

Figure 8A:
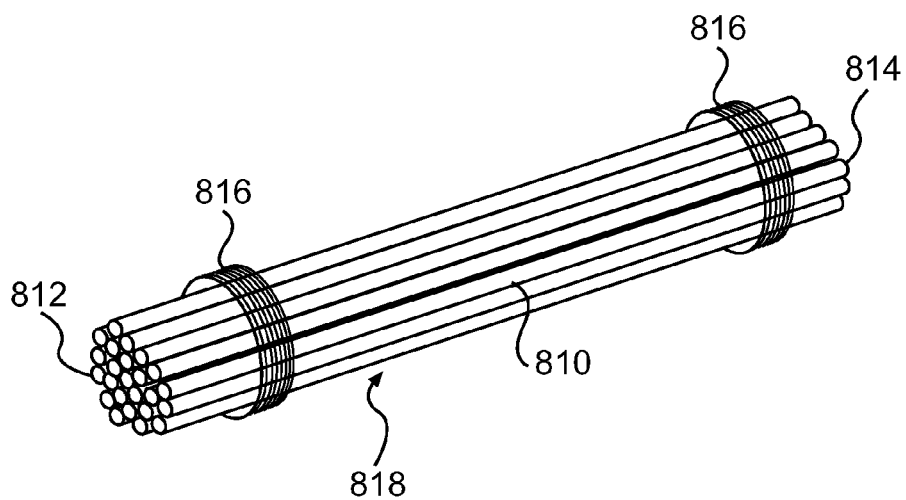
FIG. 8A illustrates a plurality of elongate non-biologic components, according to certain embodiments.

FIG. 8A illustrates a plurality of elongate non-biologic components 810. The plurality of elongate components can be bundled as a group having between 200 and 1200 individual elongate components, depending on the size and mechanical requirements of the composite graft material. In some embodiments, the number of individual components can be between 400 and 1000, 600 and 800, or approximately 700 individual components. The elongate non-biologic components may also be bioabsorbable. The plurality of elongate components 810 can have a proximal end 812 and a distal end 814. Securing elements 816 (e.g., whipping elements) can be wrapped around the plurality of components to secure the components 810 as a bundle 818. The plurality of elongate components 810 can be placed under a tensile load prior to securing. Securing elements 816 are attached to the plurality of components 810 in such a manner as to retain the preloaded tensile stress in the plurality of elongate components.

Figure 8B:
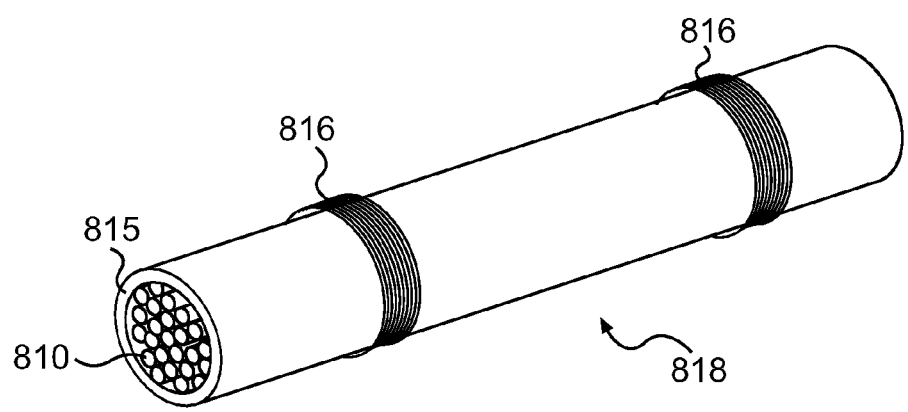
FIG. 8B illustrates a sheath of bioabsorbable material, according to certain embodiments.

FIG. 8B illustrates a non-limiting embodiment of the present disclosure, wherein sheath 815 of bioabsorbable non-biologic material is wrapped around the plurality of elongate components 810. The plurality of elongate components may be loaded with a tensile stress independently of the sheath, or the sheath and plurality of elongate components can be loaded together. Securing elements 816 can be wrapped around and over the sheath 815 of non-biologic material.

Figure 9:
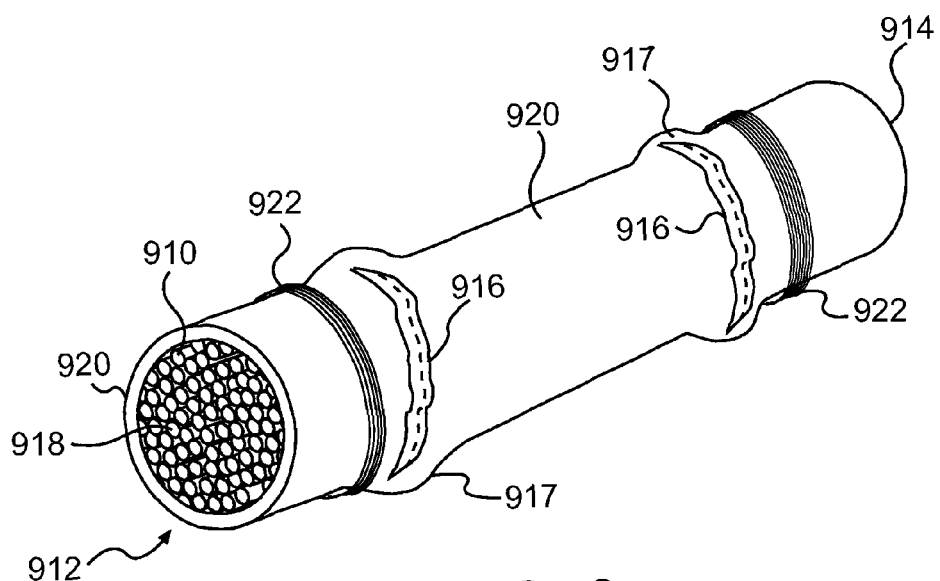
FIG. 9 illustrates a plurality of elongate non-biologic components, according to certain embodiments.

In some embodiments, a biologic component containing a biomatrix is used to cover or coat at least a portion of the plurality of elongate non-biologic components. In some embodiments, the biologic component may be in the form of a sheet wrapped around a secured plurality of elongate non-biologic components. As a non-limiting example, FIG. 9 illustrates a plurality of elongate non-biologic components 910 having a proximal end 912 and distal end 914. Securing elements 916 are wrapped around the plurality of elongate components to secure the elongate components as a bundle 918 and maintain a preloaded tensile stress in the elongate bundle 918. Securing elements 916 can be wrapped in multiple layers to form a raised surface 917.

In some embodiments, biologic component 920 may be wrapped in one or more layers around the elongate bundle 918 and secured by second securing elements 922 proximate the raised surface 917 formed by securing elements 916. Second securing elements 922 can be secured about the biologic component 920 and the elongate bundle 918 such that the biologic component is free from tensile stress. In some embodiments, the biologic component 920 can be placed under tensile stress and secured by second securing elements 922 to maintain the tensile load in the biologic component 920. In some embodiments, the tensile load in the biologic component can range from greater than 0N to about 1800N, from greater than 0 to about 600N, from about 50 to about 300N, or from about 100 to about 200N. In some embodiments, the biologic component 920 may, be pre-loaded to the same tensile stress as the plurality of elongate components 910. In some embodiments, the biologic component 920 may also be pre-loaded to tensile stress less than that of the plurality of elongate components 910. In some embodiments, the biologic component 920 can be pre-loaded to a tensile stress more than that of the plurality of elongate components 910.

In some embodiments, the biologic component can be paired with the plurality of elongate elements in a variety of ways, including: as a single layer sheet wrapped about the elongate non-biologic components; in a jellyroll manner wherein the biologic component is wrapped in multiple layers; as a non-uniform sheet such that multiple layers of biologic component are not concentric about the plurality of elongate elements; as a top sheath wrapped or coated over an inner sheath of non-biologic material; as a coating about the outer surface of the bundle of elongate non-biologic elements; and/or as a coating interspersed throughout the bundle of elongate non-biologic components.

Figure 10A:
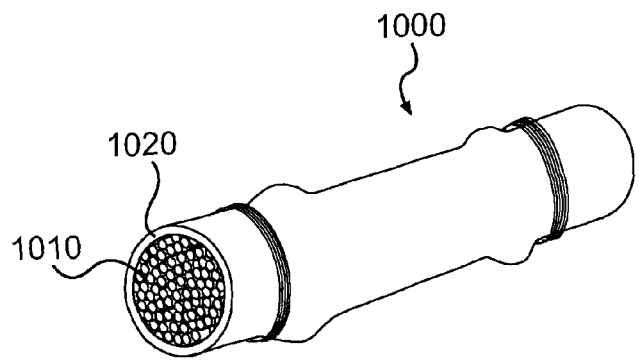
FIGS. 10A-10G illustrate exemplary embodiments of composite grafts, according to certain embodiments.
Figure 10B:
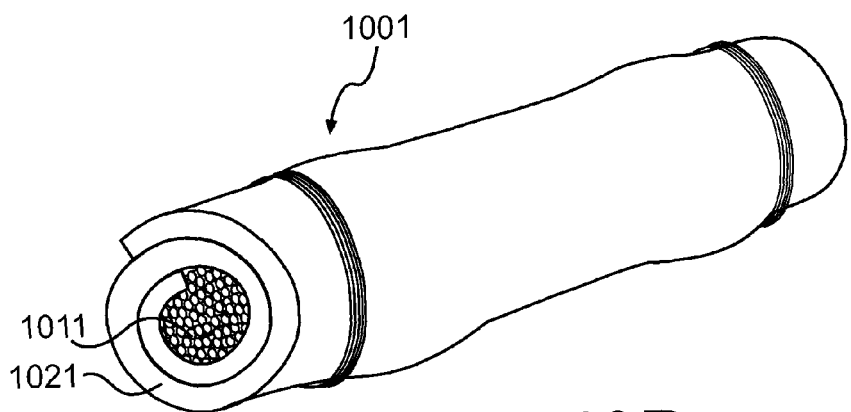
Figure 10C:
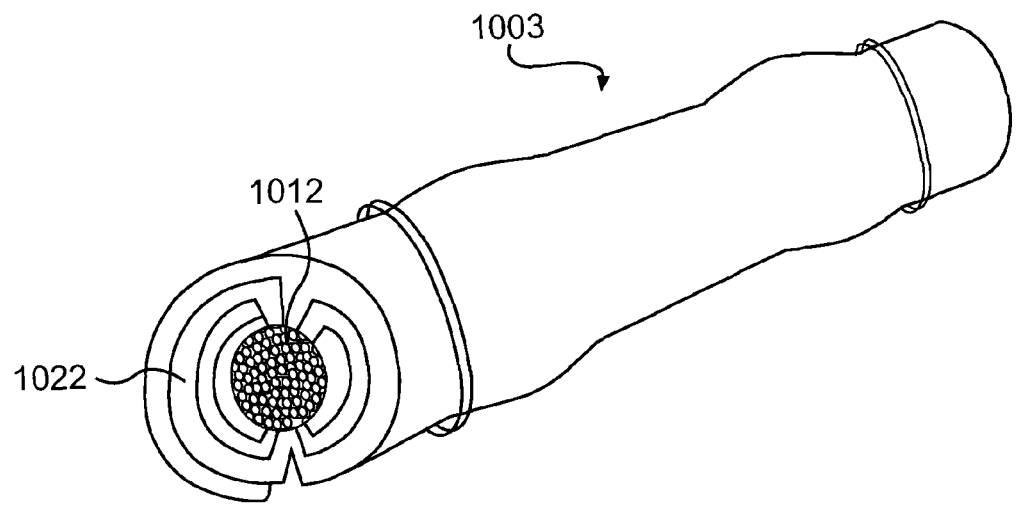
Figure 10D:
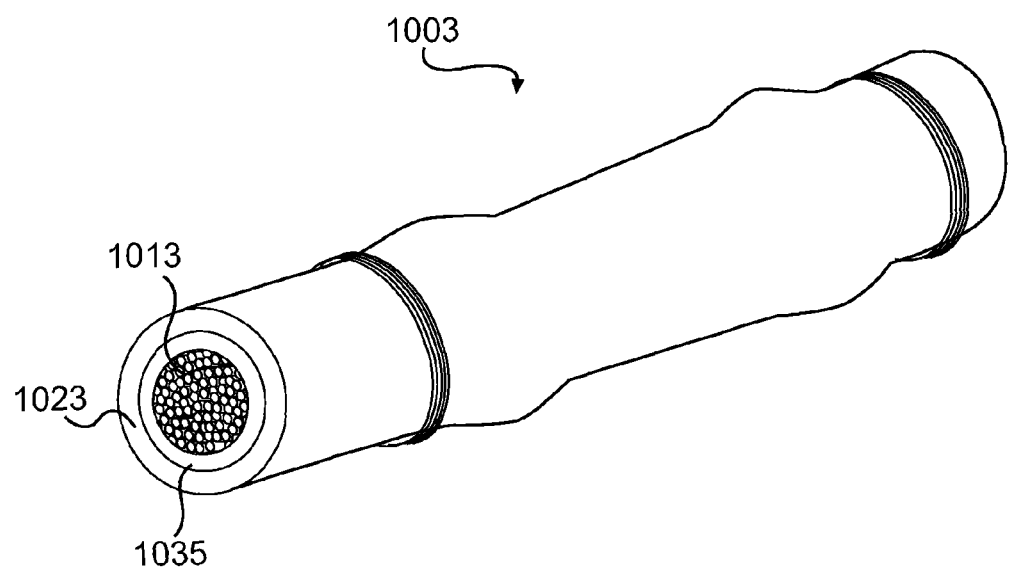

FIG. 10A shows composite graft material 1000 comprising a plurality of elongate non-biologic elements 1010 and biologic component 1020, wherein biologic component 1020 is wrapped as a sheet in a single layer over the plurality of elongate elements 1010. FIG. 10B shows a composite graft material 1001 comprising a plurality of elongate non-biologic elements 1011 and biologic component 1021, wherein biologic component 1021 is wrapped as a sheet in a jellyroll fashion with multiple layers over the plurality of elongate elements 1011. FIG. 10C shows a composite graft material 1002 comprising a plurality of elongate non-biologic elements 1012 and biologic component 1022, wherein biologic component 1022 is wrapped as a non-uniform sheet in a jellyroll fashion with multiple non-concentric layers over the plurality of elongate elements 1012. FIG. 10D shows a composite graft material 1003 comprising a plurality of elongate non-biologic elements 1013 and biologic component 1023, wherein biologic component 1023 is wrapped as a single layer sheet forming an outer sheath over inner sheath 1035 of non-biologic material. Inner sheath 1035 is wrapped about the plurality of elongate non-biologic components.

Biologic component 1020 may also be applied as a coating. The coating can, for example, be in the form of a liquid, a powder, or a spray, and may be applied using any suitable technique.

Figure 10E:
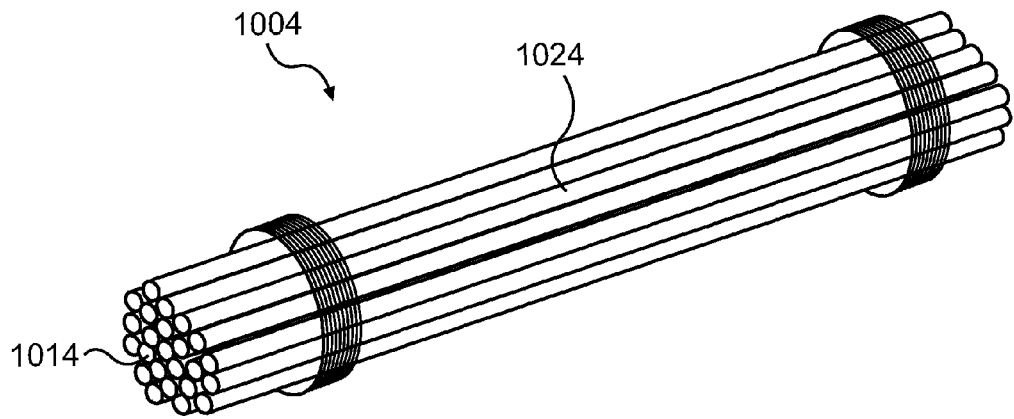
Figure 10F:
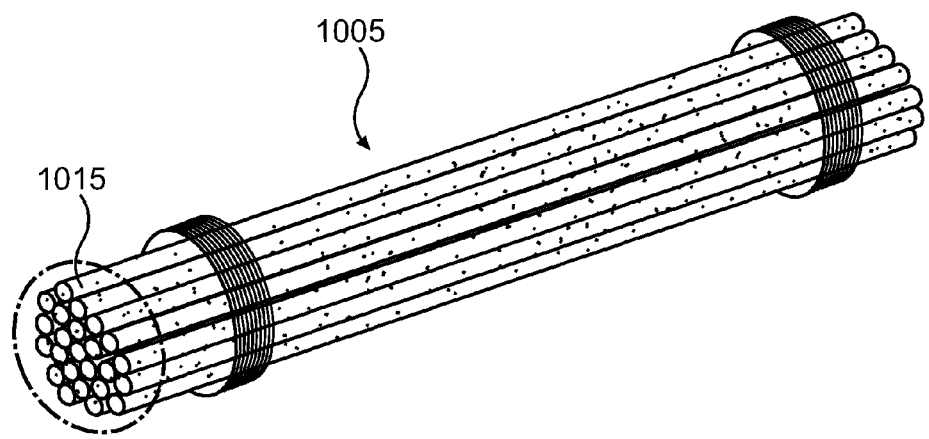
Figure 10G:
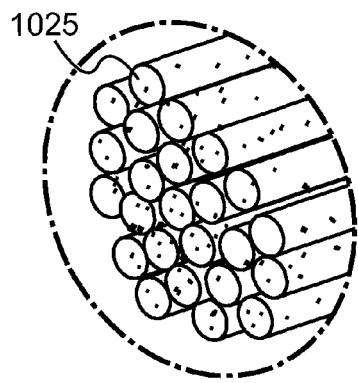

FIG. 10E shows a composite graft material 1004 comprising a plurality of elongate non-biologic elements 1014 and biologic component 1024, wherein biologic component 1024 coats the outer surface of the plurality of elongate elements 1015. FIG. 10F shows a composite graft material 1005 comprising a plurality of elongate non-biologic elements and biologic component 1025, wherein biologic component 1025 is interspersed between and coats the outer surfaces of the individual elongate elements in the plurality of elongate elements 1015, as shown in FIG. 10G.

In some embodiments, the plurality of elongate non-biologic elements are secured by a securing material (e.g., a whipping material) such that the securing material is wound about the plurality of elongate non-biologic elements in a manner that is engageable with an anchor screw. The securing material may, for example, be wound to create a screw-thread pattern having a pitch compatible with an anchoring screw to better engage and lock the composite graft material to the anchoring screw upon implantation in the patient. The material used to secure the tissue or biologic component to the plurality of elongate non-biologic elements can also be wound so as to have a screw-screw thread pattern engageable with an anchoring screw. The securing material can form the male or female thread to the threads of the anchoring screw.

In some embodiments, the composite graft material may be used for ACL replacement. In some embodiments, the composite graft material is designed to have the properties of a typical ACL, e.g., failure load (1200-2400N); stiffness (150-300 N/mm); failure stress (18-28 MPa); strain at failure (20-35%); and modulus of elasticity (75-180 MPa).

In some embodiments, the natural mechanical and biologic properties of native ACL tissue may be matched, for example, by selecting and constructing each component of a device to meet specific design requirements. For example, a device meeting the general characteristics of an ACL may be made with a non-biologic component having a modulus of elasticity of about 140 MPa, a maximum rupture load or ultimate load failure of about 1200N, and degradation resistance through 9 to 16 months before construction of the composite graft material. In some embodiments, the biologic component exhibits a modulus of elasticity of about 55 MPa at the time of implantation and a maximum load at rupture of approximately 600N before construction of the composite graft material.

In some embodiments, a composite graft material suitable for ACL repair may, for example, exhibit a maximum rupture load of approximately 1400N before implantation. In some embodiments, the ultimate failure load of the non-biologic component of such an implant may decrease after implantation, while the failure load of the biologic component will increase over time as native cells proliferate through the biomatrix. In some embodiments, the implant may have an ultimate failure load of approximately 600N within four months of implantation, approximately 400N within eight months of implantation, and approximately 1000N within 12 months of implantation. In some embodiments, the composite graft material for ACL replacement may have a stiffness of approximately 85 N/mm before implantation, approximately 106 N/mm within four months of implantation, approximately 78 N/mm within eight months of fixation, and approximately 176 N/mm within twelve months of fixation.

Figure 6:
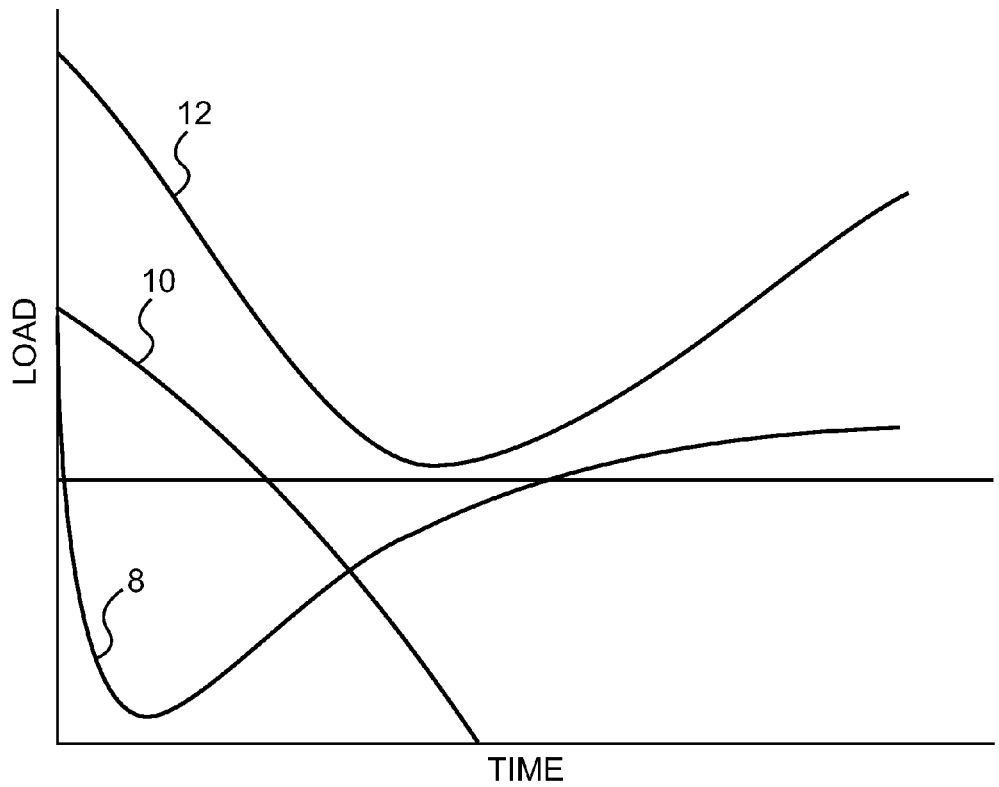
FIG. 6 is a graph depicting the load capacity over time of certain components of a composite graft material, according to certain embodiments.

FIG. 6 depicts the load capacity over time of the first component, the second component and the composite graft material of a non-limiting example of a composite ACL graft according to various embodiments. As shown, the first component, line 8, exhibited a drop in load capacity immediately following implantation with an increase in load capacity thereafter as native cells proliferated throughout the biomatrix. Line 10 illustrates the initially high load capacity of the second component after implantation with a steady decrease in load capacity as the second component degraded over time. Line 12 shows the load capacity of the composite graft containing both the first component and the second component.

Biologic Component:

Biologic components that may be suitably used to produce composite graft materials can include any biologic material (e.g., whole tissue or tissue-derived material) with the properties described herein. Non-limiting examples of such biologic materials include biomatrices, such as acellular tissue matrices.

As used herein, the term "acellular tissue matrix" ("ATM") refers to a tissue-derived biomatrix structure that is made from any of a wide range of collagen-containing tissues by removing all or substantially all viable cells and all detectable subcellular components and/or debris generated by killing cells. As used herein, an ATM lacking "substantially all viable cells" is an ATM in which the concentration of viable cells is less than 1% of that in the tissue or organ from which the ATM was made.

Accordingly, in some non-limiting embodiments, the ATMs of the present disclosure contain epithelial basement membrane. In other non-limiting embodiments, the composite grafts disclosed herein lack or substantially lack epithelial basement membrane. In some embodiments, the ATMs include a vascular basement membrane that may facilitate ingrowth of vascular endothelial cells.

ATM's suitable for use in the present disclosure may, for example, retain certain biologic functions, such as cell recognition, cell binding, the ability to support cell spreading, cell proliferation, cellular in-growth and cell differentiation. Such functions may be provided, for example, by undenatured collagenous proteins (e.g., type I collagen) and a variety of non-collagenous molecules (e.g., proteins that serve as ligands for either molecules such as integrin receptors, molecules with high charge density such as glycosaminoglycans (e.g., hyaluronan) or proteoglycans, or other adhesins). In some embodiments, the ATM's may retain certain structural functions, including maintenance of histological architecture and maintenance of the three-dimensional array of the tissue's components. The ATM's described herein may also, for example, exhibit desirable physical characteristics such as strength, elasticity, and durability, defined porosity, and retention of macromolecules.

ATMs suitable for use in the present disclosure may be crosslinked or uncrosslinked. In some non-limiting embodiments, the composite graft includes an uncrosslinked ATM. The efficiency of the biologic functions of an ATM can be measured, for example, by the ability of the ATM to support cell proliferation. In some embodiments of the present disclosure, the ATM exhibits at least 50% (e.g., at least: 50%; 60%; 70%; 80%; 90%; 95%; 98%; 99%; 99.5%; 100%; or more than 100%, or any ranges between 50%-100%) of that of the native tissue or organ from which the ATM is made.

In some embodiments, the biologic component, when implanted, is amenable to being remodeled by infiltrating cells such as differentiated cells of the relevant host tissue, stem cells such as mesenchymal stem cells, or progenitor cells. Remodeling may be directed by the above-described ATM components and signals from the surrounding host tissue (such as cytokines, extracellular matrix components, biomechanical stimuli, and bioelectrical stimuli). For example, the presence of mesenchymal stem cells in the bone marrow and the peripheral circulation has been documented in the literature and shown to regenerate a variety of musculoskeletal tissues [Caplan (1991) J. Orthop. Res. 9:641-650; Caplan (1994) Clin. Plast. Surg. 21:429-435; and Caplan et al. (1997) Clin Orthop. 342:254-269]. Additionally, in some embodiments, the graft will provide some degree (greater than threshold) of tensile and biomechanical strength during the remodeling process.

An ATM in accordance with the present disclosure may be manufactured from a variety of source tissues. For example, the ATM may be produced from any collagen-containing soft tissue and musculo-skeletonal tissue (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix. Moreover, the tissues in which the matrices containing the ATM are placed may include any tissue that can be remodeled by invading or infiltrating cells. Non-limiting examples of such tissues include skeletal tissues such as bone, cartilage, ligaments, fascia, and tendon. Other tissues in which any of the above grafts can be placed include, for example, skin, gingiva, dura, myocardium, vascular tissue, neural tissue, striated muscle, smooth muscle, bladder wall, ureter tissue, intestine, and urethra tissue.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

As an example of suitable porcine-derived tissue, non-limiting mention is Strattice™, which is a porcine dermal tissue produced by Lifecell Corp, Branchburg, N.J. The tissue matrix may be derived from porcine skin by removing the epidermis while leaving the dermal matrix substantially intact. In some embodiments, the porcine-derived tissue matrix may facilitate tissue ingrowth and remodeling with the patient's own cells. In other embodiments, the material can include a collagenous matrix derived from human cadaver skin (e.g. AlloDerm™, Lifecell Corp, Branchburg, N.J.) that has been processed to remove both the epidermis and cells.

In general, the steps involved in the production of an acellular tissue matrix include harvesting the tissue from a donor (e.g., a human cadaver or animal source) and cell removal under conditions that preserve biologic and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more a smooth muscle relaxant.

The tissue is then placed in a decellularization solution to remove viable cells (e.g., epithelial cells, endothelial cells, smooth muscle cells, and fibroblasts) from the structural matrix without damaging the biologic and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM CaCl2 and 20 mM MgCl2). Optionally, an antibiotic solution (e.g., Gentamicin) may be added to the DNase solution. Any suitable buffer can be used as long as the buffer provides suitable DNase activity.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0 In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

Particulate ATM can be made from any of the above described non-particulate ATMs by any process that results in the preservation of the biologic and structural functions described above. As used herein, particulate ATMs are those particulate or pulverized (powdered) matrices having a longest dimension of 1.0 mm or less.

In some embodiments, particulate ATM used in the present disclosure is manufactured so as to minimize damage to collagen fibers, including sheared fiber ends. As a non-limiting example of a suitable method for making particulate ATM is described in U.S. Pat. No. 6,933,326. The particle size for Cymetra is in the range of about 60 microns to about 150 microns as determined by mass spectrophotometry.

Non-Biologic Component:

The at least one non-biologic component of the present disclosure may, for example, comprise biocompatible natural and/or synthetic materials. Biocompatible natural materials may include, for example, collagen, fibrin, and silk. Biocompatible synthetic materials may include, for example, bioabsorbable polymers, non-bioabsorbable polymers, and metallic alloys or compositions. In some embodiments of the present disclosure, a non-biologic component that is biocompatible and bioabsorbable is used. Utilizing bioabsorbable polymers may allow for a transfer of loads from the non-biologic component (e.g., the polymer) to the biologic component as native tissue regenerates throughout the matrix structure of the biologic component.

As used herein, a "biocompatible" composition is one that has the ability to support cellular activity necessary for complete or partial tissue regeneration, but does not stimulate an unacceptable inflammatory or immunological response in the host. The term, "unacceptable local inflammatory or immunological response in the host" means a local or systemic inflammatory or immunologic response that prevents tissue regeneration.

As used herein, the term "bioabsorbable" means that a material can be absorbed by a mammalian body via biologically mediated degradation processes, such as enzymatic and cellular processes and/or chemically mediated degradation processes. Such processes include, for example, degradation processes wherein the degradation products are excreted through one of the body's organ systems or in which the degradation products are incorporated into normal metabolic pathways.

In some embodiments, a suitable bioabsorbable material for use in the present disclosure, is made of a poly-hydroxybutyrate (a polyhydroxyalkanoate), such as the TephaFlex polymer produced by Tepha, Inc. of Cambridge, Mass. In some embodiments, useful bioabsorbable materials include, for example, polylactic acid (PLA), polyglycolic acid (PGA), polylactideglycolide acid (PLGA), polydioxanone (PDO), or polycaprolactone (PCL). In some embodiments, bioabsorbable materials suitable for use in the present disclosure include polyanhydrides, polyorthoesters, poly(amino acids), polypeptides, polydepsipeptides, nylon-2/nylon-6copolyamides, poly(alkylene succinates), poly(hydroxyl butyrate) (PHB), poly (butylene diglocolate), poly (ε-caprolactone), polydihydropyrans, polyphosphazenes, poly (ortho ester), poly (cyano acrylates), modified polysaccharides, cellulose, starch, chitin, modified proteins, collagen, fibrin, and combinations and copolymers thereof. Non-limiting examples of non-bioabsorbable materials include noble metals such as gold, as well as the near noble metals.

In some embodiments, synthetic polymers that may be used in accordance with the present disclosure include those listed in U.S. Pat. No. 5,885,829, the disclosure of which is incorporated herein by reference in its entirety.

The non-biologic components used herein may be provided in any form. In some embodiments, the non-biologic components are in the form of a molded shape (e.g., as a single contiguous polymeric piece). Further, in some embodiments, the non-biologic components are in the form of a textile comprised of multiple yarns, the yarn being either a monofilament or a multifilament structure (such as a braid). Textile manufacturing methods can then make final structures that are knitted, woven, braided, nonwoven, or combinations thereof.

Although the present disclosure has been described with reference to certain non-limiting embodiments, other implementations are possible. For example, the composite material may be used for many applications where soft tissues need to be replaced and yet provide specific load-carrying or biomechanical characteristics, including ligament, tendon or soft tissue replacement about the knees, ankles, shoulders, neck, and spine. Other hybrid systems can be developed utilizing the same basic ideas as described above. Examples include: artificial meniscus replacement or repair; abdominal wall (e.g., hernia) repair; cartilage repair in, for example, knees, shoulders and hips; joint resurfacing (instead of removing joints, the joint articulating surface can simply be covered with a composite material reinforced with fabric using appropriately designed anchors or sutures); and pace maker pouches (a simple bag/pouch used to contain pacers or pain manager systems would make periodic replacement much simpler and would create a more stable anchor pacer implant).

Accordingly, other embodiments will be apparent to those skilled in the art from consideration of the specification disclosed herein. It is intended that the specification and embodiments disclosed herein be considered as exemplary only, with a true scope being indicated by the following claims.

What is claimed is:

1. An implantable medical device comprising:
    a plurality of first elongate non-biologic elements, at least a portion of which are under a tensile or compressive stress prior to implantation;
    at least one biologic component surrounding at least a portion of the plurality of first elongate elements;
    at least one second elongate non-biologic element, wherein the at least one second element secures at least one end portion of the plurality of first elongate non-biologic elements; and
    further comprising at least one non-biologic, bioabsorbable sheath, wherein the non-biologic, bioabsorbable sheath at least partially covers the plurality of first elongate non-biologic elements.

2. The implantable medical device of claim 1, wherein the non-biologic, bioabsorbable sheath comprises a textile material, wherein the textile material comprises a non-biologic material and has a knit, weave, braid, or nonwoven structure, or a combination thereof.

3. The implantable medical device of claim 1, wherein the at least one biologic component forms a sheath about the plurality of first elongate non-biologic elements.

4. The implantable medical device of claim 1, wherein the at least one second elongate element secures at least one end of the plurality of first elongate non-biologic elements by at least one of whipping, wrapping, and winding.

5. The implantable medical device of claim 4, wherein the at least one second elongate element forms a screw-thread pattern compatible with the threads of an anchoring screw.

6. The implantable medical device of claim 1, wherein the at least one second elongate portion comprises the same material as the plurality of first elongate non-biologic elements.

7. The implantable medical device of claim 1, wherein the plurality of first elongate non-biologic elements comprises at least one material chosen from bioabsorbable polymer, bioabsorbable metal, or a combination of bioabsorbable polymer and bioabsorbable metal.

8. The implantable medical device of claim 1, wherein the plurality of first elongate non-biologic elements comprise at least one material chosen from polyhydroxyalkanoate, polyhydroxybutyrate, polylactic acid (PLA), polyglycolic acid (PGA), polylactideglycolide acid (PLGA), polydioxanone (PDO), polycaprolactone (PCL), a polyanhydride, a polyorthoester, a poly(amino acid), a polypeptide, a polydepsipeptide, a nylon-2/nylon-6 copolyamide, a poly(alkylene succinate), poly(hydroxyl butyrate) (PHB), poly (butylene diglocolate), poly (C-caprolactone), a polydihydropyran, a polyphosphazene, a poly (cyano acrylates), modified polysaccharides, cellulose, starch, chitin, modified proteins, collagen, fibrin, and combinations and copolymers thereof.

9. The implantable medical device of claim 1, wherein the at least one biologic component comprises a biomatrix.

10. The implantable medical device of claim 9, wherein the biomatrix comprises an acellular tissue matrix or a particulate acellular tissue matrix.

11. The implantable medical device of claim 1, wherein the plurality of first elongate non-biologic elements has a higher load capacity than the at least one biologic component at the time of implantation.

12. The implantable medical device of claim 1, wherein the plurality of first elongate non-biologic elements are under a tensile stress ranging from greater than 0N to about 1800N.

13. The implantable medical device of claim 1, wherein the plurality of first elongate non-biologic elements comprises a plurality of threads, cords, cables, ribbons, or braids.

* * * * *

UNITED STATES PATENT AND TRADEMARK OFFICE
CERTIFICATE OF CORRECTION

PATENT NO. : 8,333,803 B2  
APPLICATION NO. : 12/621890  
DATED : December 18, 2012  
INVENTOR(S) : Jason Park et al.

Page 1 of 1

It is certified that error appears in the above-identified patent and that said Letters Patent is hereby corrected as shown below:

Claim 8, col. 16, line 28, "C-caprolactone)" should read --ϵ-caprolactone--.

Signed and Sealed this  
Nineteenth Day of February, 2013

Teresa Stanek Rea  
*Acting Director of the United States Patent and Trademark Office*